US006630599B1

(12) United States Patent
Singh et al.

(10) Patent No.: US 6,630,599 B1
(45) Date of Patent: Oct. 7, 2003

(54) PROCESS FOR PREPARING DERIVATIVES OF ISOPROPENYL-α, α-DIMETHYLBENZYL ISOCYANATE

(75) Inventors: Balwant Singh, Stamford; Laurence Wu-Kwang Chang, Orange, both of CT (US)

(73) Assignee: Cytec Technology Corp., Wilmington, DE (US)

( * ) Notice: Subject to any disclaimer, the term of this patent is extended or adjusted under 35 U.S.C. 154(b) by 0 days.

(21) Appl. No.: 09/223,512

(22) Filed: Dec. 30, 1998

Related U.S. Application Data

(60) Provisional application No. 60/070,534, filed on Jan. 6, 1998.

(51) Int. Cl.$^7$ ................... C07C 261/00; C07D 233/40; C07D 207/01
(52) U.S. Cl. ................... 560/25; 548/321.1; 548/537
(58) Field of Search ................... 548/537, 320; 560/25

(56) References Cited

U.S. PATENT DOCUMENTS

| 2,881,171 A | 4/1959 | Hankins | 260/256.4 |
|---|---|---|---|
| 3,366,613 A | 1/1968 | Kelley | 260/89.5 |
| 4,104,220 A | 8/1978 | Sims | 260/29.6 |
| 4,219,452 A | 8/1980 | Littlefield | 260/3 |
| 4,374,771 A * | 2/1983 | Singh et al. | 260/239.3 R |
| 4,439,616 A | 3/1984 | Singh et al. | 560/25 |
| 4,570,012 A * | 2/1986 | Singh et al. | 560/125 |
| 4,879,410 A * | 11/1989 | Singh et al. | 560/344 |
| 4,927,969 A * | 5/1990 | Kahle et al. | 564/377 |
| 5,208,347 A | 5/1993 | Parker et al. | 548/538 |
| 5,252,689 A | 10/1993 | Lucas et al. | 526/227 |
| 5,298,539 A * | 3/1994 | Singh et al. | 524/92 |
| 5,840,908 A * | 11/1998 | Singh et al. | 548/164 |

FOREIGN PATENT DOCUMENTS

| EP | 0 127 802 B1 | 4/1988 | D21H/3/38 |
|---|---|---|---|
| EP | 0 626 672 B1 | 12/1998 | G09G/3/36 |
| WO | WO 91/12243 | 8/1991 | C07D/233/06 |

* cited by examiner

*Primary Examiner*—David W. Wu
*Assistant Examiner*—Tanya Zalukaeva
(74) *Attorney, Agent, or Firm*—Valerie T. Didamo; James A. Jubinsky; Claire M. Schultz

(57) ABSTRACT

A process for preparing blocked derivatives of m- or p-isopropenyl-α,α-dimethylbenzyl isocyanates, comprising reacting a meta- or a para-isopropenyl-α,α-dimethylbenzyl carbamate ester with hydroxy functional blocking group, such as hydroxyethylene-ethyleneurea, hydroxyethylenepropylene urea, dialkylaminoethanol and dialkylamino propanol 3 Claims, No Drawings

PROCESS FOR PREPARING DERIVATIVES OF ISOPROPENYL-α, α-DIMETHYLBENZYL ISOCYANATE

This application claims benefit of provisional application Ser. No. 60/070,534 filed Jan. 6, 1998.

BACKGROUND OF THE INVENTION

1. Field of the Invention

This invention relates to a process for preparing blocked derivatives of m- or p-isopropenyl-α, α-dimethylbenzyl isocyanate (m-TMI® polymerizable isocyanate and its p-isomer), which derivatives are particularly suitable for use as wet adhesion promoters for latex polymers and paints derived therefrom. More specifically, the invention relates to the preparation of these monomers directly from in or p-isopropenyl-α,α-dimethylbenzyl carbamic acid ester which are Intermediates in the production of the corresponding Isocyanates. The invention additionally relates to the use of m- and p- isopropenyl-α,α-dimethyl benzylamines (m- and p-TMA) as adhesion promoters for latex polymers, paints, sealants and caulks.

2. Description of Related Art

EP127802 discloses producing isopropenyl-α,α-dimethylbenzyl amines (m-TMA and p-TMA) by the hydrolysis of the corresponding isocyanates, m- and p-TMI, respectfully. U.S Pat. No. 4,927,969 discloses an alternate process whereby M-TMI is reacted with ethanolamine followed by thermal cracking of the resulting hydroxyalkylurea to m-TMA and ethylene carbonate. Isopropenyl-α,α-dimethylbenzyl amines are recognized by those of ordinary skill in the art to be particularly useful as monomers which can be incorporated into polymers to introduce crosslinking sites.

The conventional method of preparing blocked derivatives of isopropenyl-α, α-dimethylbenzyl isocyanate (TMI®) involves reacting the isocyanate TMI® with an appropriate blocking group which is either an amine, a hydroxy or a lactam derivative. For example, WO91/12243 discloses reacting TMI® with an aminoethylethyleneurea (AEEU) to produce the wet adhesion monomer shown below:

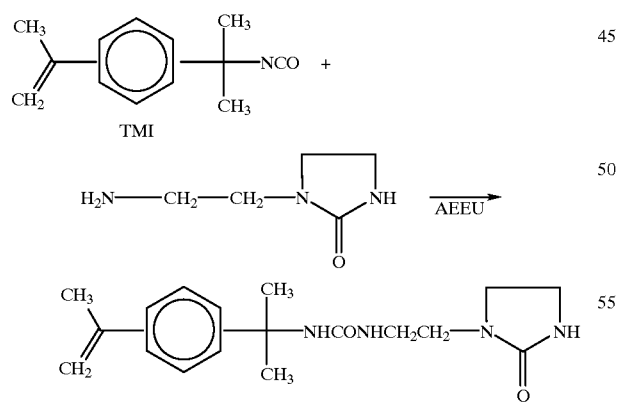

WO91/12243 discloses that this reaction is advantageously carried out in a solvent such as ethyl acetate.

U.S. Pat. Nos. 5,252,689 and 5,208,347 similarly disclose the preparation of blocked derivatives of TMI® using TMI as the staring material.

A limitation to the commercial use of blocked derivatives of TMI® has been that the conventional preparation methods, employing TMI® as the staring material, can be somewhat expensive. TMI, like other isocyanates, requires special handling procedures and the reaction with amino-functional blocking derivatives can be exothermic and thus require careful manipulation.

It has now been surprisingly discovered that certain blocked derivatives of TMI can be prepared more economically, that is, directly from the precursor m-or p-isopropenyl-α, α-dimethylbenzyl carbamate ester, by heating the precursor with an appropriate hydroxy, amino lactam or cyclic urea functional blocking group.

The monomers prepared by the process of this invention are useful to promote adhesion in polymers and copolymers, including use in aqueous emulsion copolymer latices which are used to prepare latex paints.

Latex-containing surface coatings and coating compositions having superior wet adhesion properties may therefore be produced by including in the monomer system one or a mixture of monomers produced by the present invention's novel process. Also, blends of latices modified with the monomers of the present invention may be used with unmodified latices to achieve the desired degree of wet adhesion.

It has also been discovered that wet adhesion properties can be imparted to aqueous emulsion copolymer latices by incorporating into such latices isopropenyl-α,α-dimethylbenzyl amines (m- and p-TMA).

SUMMARY OF THE INVENTION

In accordance with the present invention, there is provided a novel process for preparing blocked derivatives of isopropenyl-α,α-dimethylbenzyl isocyanate (i.e., blocked derivatives of p- or m-TMI®), comprising the step of contacting m-or p-isopropenyl-α, α-dimethylbenzyl carbamate ester with a hydroxy, an amino, a lactam or a cyclic urea functional blocking group at a temperature and for a length of time sufficient to prepare a blocked derivative of p- or m-TMI®.

The invention further provides compounds of the following general Formula I, below, as functional monomers useful for imparting wet adhesion to water based paint and coating compositions.

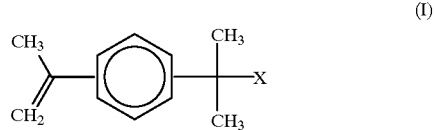

(I)

wherein X is —$NH_2$ or —NHCOZ;
wherein Z is —$NHR^1R^2$,

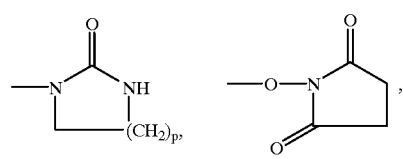

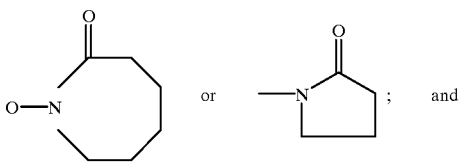
or
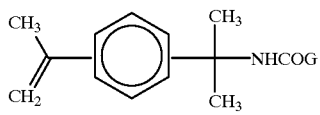
and wherein $R^1$ or $R^2$ is, individually, H or a $C_1$–$C_4$ alkyl and p is 1 or 2.

Thus, the invention is also directed to latex compositions comprising compounds of the general Formula I as wet adhesion promoters.

It is a further object of this invention to provide economically obtainable novel compounds of the Formula II, below:

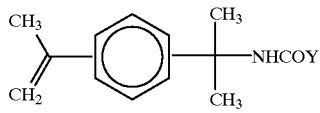 (II)

wherein Y is

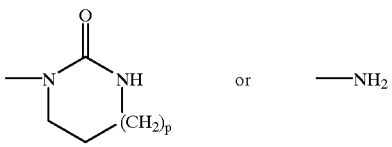 or —NH$_2$

DETAILED DESCRIPTION OF THE PREFERRED EMBODIMENTS

The present invention is a process for preparing blocked derivatives of TMI® via the direct reaction of m-or p-isopropenyl-α,α-dimethylbenzyl carbamate esters with a hydroxy, an amino, a lactam or a cyclic urea functional blocking group.

The term "TMI" in the context of the present invention, refers to isopropenyl-α, α-dimethylbenzyl isocyanate (m-TMI® polymerizable isocyanate and its p-isomer). TMI® is a commercially available product from Cytec Industries, Inc., West Paterson, N.J. Its synthesis is described in U.S. Pat. No. 4,439,616, which is herein Incorporated by reference for all purposes as if fully set forth.

The synthesis of m- and p-isopropenyl-α,α-dimethylbenzyl carbamate esters, designated as m-TMU and p-TMU, respectively, are disclosed in U.S. Pat. No. 4,439,616.

Process for Preparing Blocked Derivatives of m- and p-TMI®

This invention relates to the preparation of blocked derivatives of TMI, including compounds of the general Formula III, below:

(III)

[structure showing benzene ring with CH$_3$/CH$_2$ isopropenyl group and C(CH$_3$)$_2$—NHCOG]

wherein G is: NHR$^1$R$^2$

[structures showing various G groups including cyclic urea, alkoxy-linked cyclic urea, amide-linked cyclic urea, amine-terminated alkyl chains, and lactam groups]

wherein $R^1$ or $R^2$ is, individually, H or a $C_1$–$C_4$ alkyl, n is an integer of from 2 to 4, inclusive, p is 1 or 2 and $R^3$ is a $C_1$–$C_4$ alkyl.

The monomers of the present invention are useful as chemical intermediates. They copolymerize with many other monomers, both under solution and emulsion polymerization conditions. The polymers and copolymers are especially useful as adhesion and wet adhesion promoters.

The monomers shown in Formula III, above, are advantageously prepared by reacting m- or p-isopropenyl-α,α-dimethylbenzyl carbamate esters (i.e., m- or p-TMU) with an amino, a hydroxy, a lactam or a cyclic urea functional blocking group in the presence of heat and a suitable catalyst. The reaction is generally conducted at a temperature in the range of from about 70° C. to about 120° C. Preferably, the reaction is carried out at a temperature of between 80° and 100° C., until the removal of alcohol by-product is complete.

The resulting solid derivatives can be purified by crystallization, if desired, from a suitable solvent such as ethyl acetate, chloroform, and the like. The crude products may optionally be dissolved in appropriate solvents for further end-use applications. For example, in latex applications, the monomers may be dissolved in acrylic acid, methacrylic acid and their esters, styrene, α-methylstyrene or mixtures thereof. Monomers which are soluble in water may be supplied for end use applications in water or mixtures of water and methacrylic acid.

The 4,439,616 patent discloses the preparation of mixtures of TMU and TMXDU which are thermally cracked directly to mixtures of corresponding isocyanates, TMI and TMXDI, respectively. The patent further discloses separation of TMU from TMXDU by vacuum distillation, which may result in poor yields of TMU due to its cracking to TMI under the distillation conditions (180–200° C.). In order to obtain high yields of TMU, in pure form, for the process of the present invention, the mixture of TMU and TMXDU, produced by reacting m-diisophenylbenzene (m-DIPEB) with methyl carbamate (MeC), is neutralized, excess MeC is removed by distillation, and the solvent heptane is subsequently added to the reaction mixture. Addition of the solvent heptane results in efficient extraction of TMU from the TMXDU, since TMU preferentially dissolves in heptane. Solvents similar to heptane which may also be employed to obtain similar results, include hexane, octane, cyclohexane, and mixtures thereof.

Examples of suitable hydroxy functional blocking groups employed in the reaction include hydroxyalkylalkyleneureas such as hydroxyethylethyleneurea (HEEU) and hydroxyethylpropyleneurea (HEPU), dialkylaminoethanol and dialkylaminopropanol.

Examples of suitable amino functional blocking groups employed in the reaction include aminoalkylalkyleneureas such as aminoethylethyleneurea (AEEU) and aminoethylpropylene-urea (AEPU), N,N-dialkylaminoethylene diamine and N,N-dialkylaminopropylene diamine.

Examples of suitable lactams include pyrrolidone and caprolactam.

Examples of suitable cyclic ureas include ethylene urea and propylene urea.

The condensation reaction of TMU with an amino, a hydroxy, a lactam or a cyclic urea functional blocking group may optionally be carried out in the presence of a non-hydroxylic, non-reactive solvent. Suitable non-hydroxylic solvents include toluene, glymes, acetonitrile and dimethylformamide (DMF). Low melting, polar materials such as hydroxyethylethylene-urea (HEEU) and aminoethylethylene-eneurea (AEEU) do not require such solvents.

A catalyst is not necessary for the reaction, but, if desired, a catalyst may be added to accelerate the reaction. Examples of suitable catalysts which may be used include $ZnCl_2$, $Zn(OCOCH_3)_2$, $FeCl_3$, cobalt acetate, chelates of transition metal ions with α, β-diketones and ketoesters; titanium catalysts, such as tetraisopropyl tartrate; tin salts such as $SnCl_2$, $SnCl_4$, $SnO_2$ and tin based catalysts such as dibutyltin dilaurate, tetrabutyidlacetoxystannoxane, dimethyltin dilaurate, stannous octoate, tetrabutyl diacetoxy stannoxane (TK1® from Takeda Chemical Co.1), dibutyltin oxide and the like. The preferred catalysts are tin compounds. The amount of catalyst generally used is in the range of from about 0.1 to 5.0 mole % based on TMU. Preferably, the range of catalyst used is from about 0.2 to 0.5 mole%.

MONOMERS OF THE PRESENT INVENTION

The blocked isocyanate monomers which may be prepared by the process of the present invention are represented by the Formula III, above. Although monomers of the Formula III, wherein G is

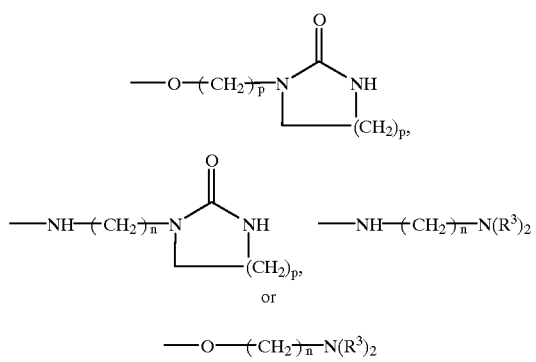

are known as wet adhesion promoters, a new method for their preparation has herein been discovered. Additionally-although the compounds of Formula III, wherein G is ,

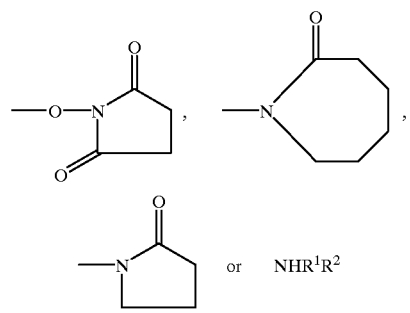

are known compounds which can be made by the present invention's novel process, their use as wet adhesion promoters has herein been discovered.

Furthermore, compounds of the general Formula II, wherein Y is $NH_2$ or

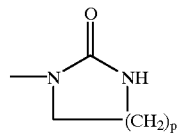

which may also be prepared by the novel process of the present invention, have herein been discovered as novel compounds, useful as wet adhesion promoters.

Although compounds of the Formula I, wherein X is —$NH_2$, that is, m- and p-isopropenyl α,α-dimethylbenzylamines (m- and p-TMA), are known compounds, not produced by the present invention's novel process, their use as wet adhesion promoters has herein been discovered.

Representative examples of the monomers which have herein been discovered to function as useful wet adhesion promoters are listed below. m- and p-isopropenyl-α,α-dimethylbenzyl amines (m- and p-TMAs), N-hydroxysuccinimide blocked TMI, hydroxyethylethyleneurea-blocked TMI, aminoethylethyleneurea-blocked TMI, N,N-diethylethylene diamine-blocked TMI and ammonia-blocked TMI.

It has also been discovered that blocked derivatives of m- and p-TMI may also be prepared by reacting m- and p-diisopropenyl benzenes, respectively with urea or urethane derivative of the blocking groups in the presence of acid catalyst such as p-TSA, $H_2SO_4$, etc. This is illustrated by the synthesis of pyrrolidone blocked m-TMI (monomer M11) from m- diisopropenyl benzene and pyrrolidone urea (N-carbamyl pyrrolidone).

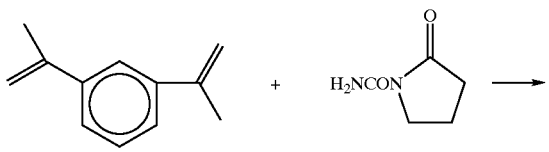

-continued

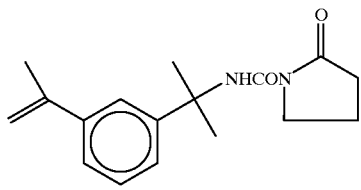

Uses of the Monomers of the Present Invention

The monomers of the present invention find use, for example, in adhesives, caulks, sealants, coatings, wood coatings, can coatings, paper coatings, marine coatings, architectural coatings, automotive coatings, non-wovens, binders, wett/dry strength resins for paper, textiles, lubricants, modifiers for cement, mortar and concrete, intercoat adhesion promoters, polymer compatibilizers, pressure sensitive adhesives, primers, surface modifiers, corrosion inhibitors and formaldehyde scavengers. A particularly preferred use of the monomers of the present invention is as wet adhesion promoters.

The monomers of the present invention are polymerizable or copolymerizable through the unsaturation in the compounds. They may be used as comonomers in monomeric systems for forming aqueous emulsion polymers, including in compositions comprising monomers such as acrylics, vinyls, vinylacrylics, vinylaromatics, α,β-unsaturated carboxylic acids and their esters, as well as other known specialty monomers. Examples of suitable acrylic monomers include methyl acrylate, ethyl acrylate, methyl methacrylate, hydroxyalkyl acrylates, hydroxyalkyl methacrylates, butyl acrylate, hexyl acrylate, cyclohexyl acrylate, 2-hydroxyethyl methacrylate, 2-ethylhexylacrylate, 2-hydroxyethylacrylate, 2-hydroxypropyl methacrylate, 2-hydroxypropyl acrylate, piperidinoethyl methacrylate, morpholinoethyl methacrylate, and the like.

Examples of suitable vinyl monomers include ethylene, propylene, butylene, isobutylene, hexene, vinyl acetate, vinyl esters of versatic acid (i.e., VEOVA -9 and VEOVA -10), vinyl chloride, acrylonitrile, acrylamide, methacrylamide, vinylidene chloride, oleic acid, linoleic acid, 1,3-butadiene, isoprene, norbornene, cyclopentadlene and the like.

Examples of useful unsaturated carboxylic acids include itaconic acid, citraconic acid, crotonic acid, mesaconic acid, maleic acid, fumaric acid, and the like; α,β-unsaturated dicarboxylic acid esters of the dicarboxylic acids described above including aromatic esters, cycloalkyl esters, alkyl esters, hydroxyalkyl esters, alkoxy alkyl esters, and the like.

Examples of suitable vinyl aromatic monomers, with which the present invention's monomers can be polymerized, include styrene, α-methylstyrene, vinyltoluene, ethylstyrene, isopropylstyrene, p-hydroxystyrene, p-acetoxystyrene, p-chlorostyrene and p-chloromethyl-styrene.

In particular, the monomers of this invention may be incorporated in effective amounts in aqueous polymer systems to enhance the wet adhesion of paints made from the polymers. Maleuric, fumauric, citraconuric, itaconuric acids and their alkyl esters may also be incorporated in effective amounts in aqueous polymer systems to enhance the wet adhesion properties of paint compositions.

The emulsion polymers used in formulating latex paints usually are all acrylic copolymers comprising alkyl esters of acrylic and methacrylic acid with minor amounts of acrylic acid, methacrylic acid, acrylamide or methacrylamide, or they are vinyl/acrylic polymers comprising vinyl containing monomers or polymers in combination with softer acrylic monomers. The commonly used ethylenically unsaturated monomers in making acrylic paints are butyl acrylate, methyl methacrylate, ethyl acrylate, 2-ethyl hexyl acrylate, and mixtures thereof. In acrylic paint compositions at least 50% of the polymer formed is comprised of an ester of acrylic or methacrylic acid. The vinyl-acrylic paints usually include ethylenically unsaturated monomers such as vinyl acetate and butyl acrylate or 2-ethylhexyl acrylate. In vinyl acrylic paint compositions, at least 50% of the polymer formed is comprised of vinyl acetate, with the remainder being selected from the esters of acrylic or methacrylic acid.

The monomers of this invention may be added to a monomer composition from which acrylic or vinyl acrylic polymers are formed in a concentration which may vary over a wide range. Preferably the concentration is at least sufficient to improve the wet adhesion of paints made from the polymer composition. Concentrations may range from about 0.05% to about 20%, by weight, based on the total weight of monomers. Preferably, the concentration is in the range of from about 0.1% to about 5.0%, and more preferably from about 0.5% to about 3.0%.

The monomer composition may be used in conjunction with other ongredients, such as various free radical catalysts to initiate polymerization, emulsifying agents to protect particles from agglomeration, and buffers to maintain a desired pH during polymerization, as is generally well-known to those of ordinary skill in the art of polymerization. For example, suitable free radical polymerization catalysts are the catalysts known to promote emulsion polymerization and include water-soluble oxidizing agents such as organic peroxides (e.g., t-butyl hydroperoxide, cumene hydroperoxide, etc.), inorganic oxidizing agents (e.g., hydrogen peroxide, potassium persulfate, sodium persulfate, ammonium persulfate, etc.) and those catalysts that are activated in the water phase by a water-soluble reducing agent. Such catalysts are employed in a catalytic amount sufficient to cause polymerization. Generally, a catalytic amount ranges from about 0.01 to 5.0 parts per hundred parts of monomer. As alternatives to heat and catalytic compounds to activate polymerization, other free radical producing means, such as exposure to activating radiations, can be employed.

Suitable emulsifying agents include anionic, cationic, and nonionic emulsifiers customarily used in emulsion polymerization. Usually, at least one anionic emulsifier is utilized and one or more nonionic emulsifiers may also be utilized. Representative anionic emulsifiers are the esters of sulfosuccinic acid, amides of sulfosuccinic acid, alkyl aryl sulfonates, alkali metal alkyl sulfates, the sulfonated alkyl esters and fatty acid soaps. The emulsifying agents are employed in amounts to achieve adequate emulsification and to provide desired particle size and particle size distribution.

Examples of suitable buffers used to maintain a desired pH during polymerization include ingredients such as acids, salts, chain transfer agents and chelating agents. For example, if the polymerization constituents include a mono-ethylenically unsaturated carboxylic acid comonomer, polymerization under acidic conditions (pH 2–7, preferably 2–5) is preferred. In such instances, the aqueous medium can include those known weak acids and their salts that are commonly used to provide a buffered system at the desired pH range.

The manner of combining the polymerization ingredients can be various known monomer feed methods, such as, continuous monomer addition, incremental monomer addition, or addition in a single charge of the entire amount of monomers. The entire amount of the aqueous medium with polymerization additives can be present on the polymerization vessel before introduction of the monomer, or alternatively, the aqueous medium, or a portion of it, can be added continuously or incrementally during the course of the polymerization.

The polymerization of the monomer system which includes ethylenically unsaturated monomers and either one or more of the the novel monomers of the present invention can be accomplished by known procedures for polymerization in aqueous emulsions, as disclosed, for example, in U.S. Pat. Nos. 3,366,613; 4,104,220; 2,881,171; 4,219,452 and EPO 626672A2, which are incorporated by reference herein for all purposes as if fully set forth. Pre-polymer monomeric starting materials used to form polymeric pre-emulsion compositions using the monomers of the present invention are typically dissolved or suspended in the aqueous medium to a desired concentration. Preferably, the polymerization of the invention is performed at a concentration range of about 10 weight-% to about 70 weight-% of the monomers in the aqueous medium, although somewhat higher or lower concentrations may be employed in some cases.

By way of example, polymerization is initiated by heating the emulsified mixture with continued agitation to a temperature usually between about 500C to about 11 00C, preferably between 60° C. to about 100° C. Heating of the emulsified mixture is also preferably conducted in an inert atmosphere (e.g., purging with nitrogen, argon, etc.). Polymerization is continued by maintaining the emulsified mixture at the desired temperature until conversion of the monomer or monomers to polymer has been reached.

Generally, depending upon the final application of the polymeric composition, the polymer may contain anywhere from about 0.05 weight-% to about 20.0 weight-% of the monomer of the present invention (based on the concentration of the monomer), preferably from about 0.1% to about 5.0 weight-% of the present monomer, and more preferably from about 0.5% to about 3.0 weight-% of the monomer of the present invention.

In addition to making emulsion polymers, it is contemplated that the monomers of the present invention be used to form solution copolymers. Polymerization towards the formulation of solution polymers may be completed under substantially similar circumstances as described above for emulsion polymerization except that the medium of polymerization in a solution polymerization reaction is organic instead of aqueous. Generally, the solution polymerization reaction is carried out with the monomers in solution in an inert organic solvent such as tetrahydrofuran, methyl ethyl ketone, acetone, ethyl acetate, or other suitable organic solvents such as hexane, heptane, octane, toluene, xylene and mixtures thereof. In the case of water-soluble monomers, inverse emulsions may also be prepared. Inverse emulsion being defined as a water-soluble polymer system dispersed in an organic solvent. Preferred solvents are non-toxic and odorless.

The invention will now be illustrated by the following examples. The examples are not intended to be limiting of the scope of the present invention. In conjunction with the general and detailed descriptions above, the examples provide further understanding of the present invention.

EXAMPLE A

Hydroxyethylethyleneurea (HEEU)

A mixture of 93.3 g of 2-(2-aminoethylamino) ethanol (0.9 moles) and 52.1 g of urea (0.87 moles) was heated slowly to 230° C. with stirring. The evolution of ammonia began when the temperature reached 130° C. The reaction mixture was heated at 230° C. for 2 hours. The mixture solidified to a light-yellow solid after it had cooled to room temperature to afford 110.5 g of hydroxyethylethyleneurea. Recrystallized from acetone, M.P.: 55–57.50° C.; [1] H NMR (DMSO-$d_6$): d 6.3 (s, 1 H), 4.6 (s, 1 H), 3.5–3.0 (m, 8 H).

EXAMPLE B

Aminoethylethyleneurea (AEEU)

A mixture of 206.4 g of diethylenetriamine (2 moles) and 117.0 g of urea (1.95 moles) was slowly heated to 210° C. The evolution of ammonia began when the temperature of the reaction mixture reached 130° C. The reaction mixture was then held at 210° C. for 3 hours before it was distilled under vacuum to afford 132 g of aminoethylethyleneurea. B.P.: 175° C. (1.5 mm); [1] H NMR (DMSO-$d_6$): d 6.3 (s, 1 H), 3.4–2.5 (m, 8 H), 1.4 (s, 1 H).

EXAMPLE I

Synthesis of m-isopropenyl-$\alpha,\alpha$-dimethylbenzylamine (m-TMA) from m-TMU Monomer M1

A mixture of 259 g (1.11 moles) of m-TMU (m-isopropenyl-$\alpha,\alpha$-dimethylbenzyl carbamic acid, methyl ester), 165 g of 87.6% (2.58 moles) potassium hydroxide, and 460 ml of methyl cellosolve was refluxed for 5 hours. The solvent was removed under reduced pressure and the residue was mixed with 700 ml of methylene chloride. The methylene chloride solution was filtered, and the filtrate was washed twice with water, dried over potassium carbonate and distilled. A total of 162 g of m-TMA was collected in 88% yield, b.p.: 102° C., 2 mm Hg. [1] H NMR (CDCl$_3$): $\delta$7.2–7.6 (m, 4 H); 5.35 (s, 1 H); 5.10 (s, 3 H); 2.5–2.6 (B, 2 H); 2.5 (s, 6 H).

EXAMPLE II

Synthesis of m-TMI Urea (Ammonia Blocked m-TMI)

Monomer M2

To a solution of 20.97 g (0.104 mole) M-TMI and 35 ml acetonitrile was added dropwise 14.36 g (0.123 mole) 30% aqueous ammonium hydroxide. The reaction mixture, a white slurry, was stirred at room temperature for 1 hr and then filtered. The collected solid was washed with water and vaccum dried (400° C.). The dry solid weighed 22.2 g. M.P.: 127°–132° C., H[1]-NMR (CDCl$_3$): $\delta$7.2–7.6 (m, 4 H); 5.6 (bs, 1 H); 5.35 (s, 1 H); 5.10 (s, 1 H); 4.4 (s, 3 H); 1.6 (s, 6 H).

EXAMPLE III

Reaction of m-TMU with N, N-Diethylethylene diamine

Monomer M3

A mixture of 2.33 g (0.01 mole) of m-TMU, 1.16 (0.01 mole) of N, N-diethylethylene diamine, 80 mg of TK-1 tin catalyst was heated at 140° C. under 30 mm Hg pressure for 3 hours. The methanol coproduced in the reaction mixture was condensed in a dry-Ice/acetone trap. The reaction mixture was cooled to room temperature and dissolved in 20 ml of chloroform. The chloroform solution was filtered, washed with water and dried over potassium carbonate. Removal of solvent left a solid residue which was recrystallized from ethyl acetate to obtain 2.2 gm (70%) of N,N-diethylethylene diamine-blocked m-TMI. M.P.: 60°–63° C.; $H^1$-NMR (CDCl$_3$): δ7.2–7.6 (m, 4 H); 5.3–5.5 (m, 2 H); 5.08 (s, 1 H); 4.9 (s, 1 H); 3.0–3.2 (m, 2 H); 2.2–2.25 (m, 2 H); 2.18 (s, 1 H); 2.0 (s, 6 H); 1.6 (s, 6 H).

EXAMPLE IV

Reaction of m-TMU with N,N-Dimethylaminoethanol

Monomer M4

The reaction procedure of Example III may be used, except that m-TMU and N, N-dimethylaminoethanol are used for the synthesis.

EXAMPLE V

Reaction of m-TMU with N, N-Dimethylethylenediamine

Monomer M5

The reaction procedure for synthesis of Example III may be used, except that m-TMU and N, N-dimethylethylenediamine are used.

EXAMPLE VI

Reaction of m-TMU with Ethyleneurea

Monomer M6

The reaction procedure of Example III is used, except 10.54 g (0.045 mole) m-TMU, 4.1 g (0.048 mole) ethyleneurea, and 0.24 g of TK-1 is used for the synthesis. The expected ethyleneurea-blocked m-TMI yield is about 60%.

EXAMLE VII

Reaction of m-TMU with 2-hydroxethylethylene urea (HEEU)

Monomer M7

A mixture of 6.99 g (0.03 mole) m-TMU, 5.85 g (0.045 mole) HEEU, 77 mg TK-1 tin catalyst (1,3-dlacetoxy 1,1, 3,3-tetrabutyl distannoxane) and 77 mg didecylmethylamine (DAMA-10) was heated at 135° C. under vaccum for 6 hrs. The reaction mixture was allowed to cool and then dissolved in ethyl acetate. The ethyl acetate solution was washed with water, dried over magnesium sulfate. Removal of ethyl acetate left 8.6 g of a solid residue. M.P.: 128°–131° C., $H^1$-NMR (CDCl$_3$): δ72–7.6 (m, 4 H); 5.45 (s, 1 H); 5.35 (s, 1 H); 5.25 (s, 1 H) 5.10 (s, 1 H); 4.0–4.2 (t. 2 H); 3.2–3.6 (m, 6 H); 2.15 (s, 3 H); 2.0 (s, 6 H).

EXAMPLE VIII

Reaction of m-TMU with Aminoethylethyleneurea (AEEU)

Monomer M8

A mixture of 3.0 g (0.013 moles) m-TMU, 1.93 g (0.015 mole) AEEU and 80 mg TK-1 tin catalyst was heated in a 140° C. bath under 30 mm Hg pressure for 3 hrs. The reaction mixture was allowed to cool and then dissolved in 20 ml of chloroform. The chloroform solution was extracted with 20 ml of water and dried over potassium carbonate. Removal of solvent left a white solid residue which weighed 3.5 g, 83% yield. M.P.: 120°–125° C.; $^1$H-NMR (CDCl$_3$): δ7.2–7.6 (m, 4 H); 5.55 (s, 1 H); 5.4 (s, 1 H); 5.0–5.2 (m, 2 H); 4.8 (s, 1 H); 3.0–3.4 (m, 8 H); 2.15 (s, 3 H); 1.6 (s, 6 H).

EXAMPLE IX

Reaction of m-TMU with N-Hydroxysuccinimide

Monomer M9

The reaction procedure is the same as that of Example VIII except that m-TMU and N-hydroxysuccinimide are used for the synthesis. The expected yield of N-hydroxysuccinimide blocked m-TMI having a M.P.:135°–137° C. is 60% based on m-TMU.

EXAMPLE X

Reaction of m-TMU with ε-Caprolactam

Monomer M10

The reaction procedure is the same as that of Example XI except m-TMU and ε-caprolactam is used for the synthesis. The expected yield of ε-caprolactam-blocked m-TMI M.P.: 63°–65° C. is 43% based on m-TMU.

EXAMPLE XI

Reaction of m-TMU with 2-Pyrrolidone Pyrrolidone Blocked m-TMI

Monomer M11

A mixture of 7.67 g (0.0329 mole) m-TMU, 28.0 g (0.0329 mole) pyrrolidone, 0.077 g DAMA-10 (didecylmethylamine), 0.077 g dibutyltbn dilaurate (T-12), 0.036 g 4-methoxyphenol was heated at 140° C. under 50 mm Hg pressure for 6 hours with continuous removal of methanol which was collected in a dry ice-acetone trap. The reaction mixture was allowed to cool to 100° C. and excess 2-pyrrolidone was removed under reduced pressure. The residue was washed with water, and vacuum dried to yield the product as a pale yellow solid; M.P.: 48°–55° C., yield: 83%.

EXAMPLE XI A

Synthesis of Pyrrolidone Blocked m-TMI from Pyrrolidone Urea

Monomer M11

(a) Synthesis of Pyrrolidone Urea

A mixture containing 50 g (0.67 mole) of methyl carbamate, 272 g (3.20 moles) of pyrrolidone, 2.4 g of TK-1 tin catalyst, and 2.4 g of DAMA-10 was heated at 140° C. under 40–50 mm Hg pressure for 3.5 hours. The methanol produced by the reaction was collected in a dry ice-acetone trap during the reaction. The reaction mixture was then analyzed with GLC (internal standard method). The results indicated that the yield of pyrrolidone urea was 85% based on methyl carbamate charged, and 10% of the starting methyl carbamate still remained in the reaction mixture. The reaction mixture was then distilled under reduced pressure to remove excess pyrrolidone and the remaining methyl carbamate. The residue was stirred with 200 ml of toluene for 15 minutes and filtered. The collected solid was washed with toluene and air-dried to afford 46 g (54%) of the desired product; mp 142°–144° C. (lit. mp 142°–143° C.); IR (cm$^{-1}$): 3360, 1710, 1660, 1590, 1370, 1250; $^1$H-NMR (CDCl$_3$): δ8.2 (s, 1 H), 5.9 (s, 1 H), 3.9 (t, 2 H), 2.6 (t, 2 H), 2.1 (t, 2 H).

(b) Reaction of Pyrrolidone urea with m-diisopropenylbenzene

A solution of 101.1 g (0.789 mole) pyrrolidone urea (Example XI A) and 5.32 g p-toluene sulfonic acid in 398 ml of acetonitrile was heated to 65° C. Fifty grams (0.316 mole) of m-diisopropenylbenzene (m-DIPEB) was metered into the solution over a 3-hour period. The reaction mixture was heated for an additional 3 hours and allowed to cool. The reaction mixture was neutralized with 4.5 ml of 10 N sodium hydroxide, stirred for 15 minutes and filtered. Acetonitrile was removed under reduced pressure, and the residue was stirred with 300 ml of toluene and then filtered to remove excess pyrrolidone urea. The toluene filtrate was distilled to remove toluene and m-DIPEB. The distillation residue was then extracted with heptane to yield 46.1 g BTMI (51% yield). M.P.: 48°–52° C.

These Examples illustrate the utility of the monomers of the present invention in wet ashesion applications.

TEST PROCEDURE

A. Latex Preparation

The following general procedure was used in the synthesis of all acrylic latexes containing the monomers of the present invention. The wet adhesion monomer (WAM) used in the preparation of the acrylic latexes was either a monomer of the present invention or, alternatively, a commerically available wet adhesion monomer.

A 1-liter glass jacketed resin reactor with a bottom discharge valve is used. The reactor is equipped with thermometer, a circulating constant temperature heating bath, $N_2$ purge, a Teflon turbin agitator, a monomer emulsion feed pump calibrated for 4.59 grams/min and an initiator feed pump calibrated for 0.5 g/min.

The following charge is used:

|  | Wt. (g) |
|---|---|
| Reactor Charge | |
| D.I. Water | 192.1 |
| Monomer Emulsion | |
| D.I. Water | 182.6 |
| Surfactant* (real basis) | 4.7 |
| Wet Adhesion Monomer (WAM) | 5.0 |
| Methylmethacrylate | 260.0 |
| Butylacrylate | 230.0 |
| Methacryiic acid | 2.7 |
| Initiator Solution | |
| Ammonium Persulfate | 2.0 |
| D.I. Water | 98.0 |

Aerosol ® 102 (Cytec Industries Inc.) or Rhodacal ® DS4 (*23% solution in water; product of Rhone-Poulenc Co.)

The Monomer Emulsion is Prepared as Follows:
1. Dissolve the surfactant in water.
2. If the WAM monomer is only water soluble, add it to the water surfactant solution.
3. Blend all the monomers together. If the WAM monomer is soluble in the organic phase, dissolve it in the monomer.
4. Finally, mix the monomers with the water surfactant solution and keep the mixture agitated to insure a homogeneous dispersion.

B. Polymerization Procedure

1. Heat the reactor water to 80° C. while the system is under a $N_2$ blanket.
2. At 80° C. add 25 grams of initiator solution and 14.2 grams of monomer emulsion. Hold at ~80° C. for 15 minutes.
3. Feed the remainder of the monomer emulsion and initiator solutions over a 2.5 hour period using the appropriate calibrated pumps. Maintain a polymerization temperature of 80±1° C.
4. After completion of the monomer and initiator addition, heat to 85° C. for 30 minutes.
5. Cool the emulsion to 23°–25° C. and adjust the pH to 9.0±0.2 with 28% $NH_4OH$. Filter the emulsion through a cheesecloth paint filter.

The yield should be ~955 grams, a viscosity of 20–28 cps and solids of ~50%.

C. Wet Adhesion Test

The wet adhesion test is a version of the scrub resistance test described in the ASTM procedure #D2486.

Using a 7 mil Dow bar, cast a film of Glidden Glid-Guard® 4554 glass alkyd on a Leneta scrub panel. Age the panels for a minimum of 21 days, but not more than 6 weeks prior to use. Apply the test paint with a 7 mil Dow blade over the aged alkyd and air dry 4 hours, 24 hours and seven days. Cross-hatch the test paint in a grid of 0.25 inch (0.65 mm) squares using a razor knife and template. Soak the panel in room temperature water for 30 minutes and record any blistering or edge lift. If there is no blistering or edge lift from the water soak, place the panel on the scrub machine (described in ASTM procedure D2486). Add 20 ml of 5% "LAVA" soap slurry and 5 ml of water to the panel. Scrub the scored area, add more water if the panel becomes dry. Record the percentage of the squares removed after 1000 cycles.

The physical properties of some of the latexes prepared using the monomers of the present invention are summarized in Table I, below. Included for comparison are latexes containing no wet adhesion monomer, which control is indicated as sample "L-C," and commercially available SIPOMER® WAM II, indicated as sample "L-WII." The labels M1, M3, etc. refer to monomers corresponding to the Examples described herein. All wet adhesion monomers were tested at 1 wt % level based on the final latex polymer.

TABLE I

| | | | | | | Physical Properties |
|---|---|---|---|---|---|---|
| Example | Sample | Monomer | Wt % | pH | % Solids | Particle Size (Microns) |
| 12 | L-C | None | — | 9.02 | 49.3 | 0.21–0.25 |
| 13 | L-WII | SIPOMER ® WAM II | (1.0) | 9.03 | 51.2 | 0.21–0.25 |
| 14 | L-WII | WAM II | (0.5) | 9.11 | 50.5 | 0.21–0.25 |
| 15 | L-M1 | M1 | (1.0) | 9.06 | 49.9 | 0.21–0.25 |
| 16 | L-M1 | M1 | (0.5) | 9.06 | 49.1 | 0.21–0.25 |
| 17 | L-M1 | M1 | (0.1) | 9.02 | 50.6 | 0.21–0.25 |
| 18 | L-M2 | M2 | (1.0) | 9.01 | 50.0 | 0.21–0.25 |
| 19 | L-M3 | M3 | (1.0) | 9.05 | 49.8 | 0.21–0.25 |
| 20 | L-M4 | M4 | (1.0) | 8.99 | 50.1 | 0.21–0.25 |
| 21 | L-M6 | M6 | (1.0) | 9.01 | 50.10 | 0.21–0.25 |
| 22 | L-M7 | M7 | (1.0) | 9.06 | 50.0 | 0.21–0.25 |
| 23 | L-M8 | M8 | (1.0) | 9.05 | 49.95 | 0.21–0.25 |
| 24 | L-M9 | M9 | (1.0) | 9.04 | 50.0 | 0.21–0.25 |
| 25 | L-M10 | M10 | (1.0) | 9.01 | 50.3 | 0.21–0.25 |

The above latexes were formulated into semigloss latex exterior house paint for measurement of wet adhesion properties. The recipe used for the paint formulation is shown below in Table II. The results of the wet adhesion properties are shown in Table IV, below.

TABLE II

| Paint | Wt. |
|---|---|
| Water | 166.6 |
| Polyphobe 102 | 8.8 |
| Amp 95 | 3.0 |
| Nuosept 95 | 2.3 |
| Propylene glycol | 60.5 |
| Colloid 286 | 7.4 |
| Colloid 653 | 1.9 |
| Triton N-57 | 2.1 |
| Tronox CR-828 | 250.0 |
| Attagel 50 | 2.0 |
| Grind | |
| Water | 73.7 |
| Polyphobe 102 | 13.2 |
| Water | 12.5 |
| Latex | 420.8 |
| UCAR Filmer IBT | 10.5 |
| Colloid 653 | 2.8 |
| Polyphase AF-1 | 7.3 |
| Triton GR-7M | 1.1 |
| Totals | 1052.5 |

Table III identifies the various ingredients used in the paint formulation. The ingredients are added in the order listed to a high speed paint disperser.

TABLE III

EXTERIOR TRIM HOUSE PAINT

| PAINT | DESCRIPTION |
|---|---|
| Add in | |
| order to high speed disperser | |
| Water | |
| Polyphobe 102 | Rheology Modifier |
| Amp 95 | Amine, 2-Amino-2-Methyl Propanol |
| Nuosept 95 | In can preservative, bicyclic oxazolidines |
| Propylene Glycol | Open Time |
| Colloid 280 | Dispersant, Ammonium Polyacrylic Copolymer Solution |
| Colloid 653 | Defoamer, Hydrophobic Silica Defoamer |
| Triton N-67 | Nonionic Surfactant |
| Tronox CR-828 | Titanium Dioxide |
| Attagel 50 | Attapulgite Clay |
| Grind 20 minutes | |
| Add the following in order | |
| Water | |
| Polyphobe 102 | Rheology Modifier |
| Water | |
| Latex | |
| UCAR Filmer IBT | Coalescent Solvent, Ester Alcohol |
| Colloid 653 | Defoamer, Hydrophobic Silica Defoamer |
| Polyphase AF-1 | Mildewcide, 3 Iodo-2Propynyl Butyl Carbamate |
| Triton GR-7M | Anionic Surfactant, Dioctyl Sodium Sulfosuccinate |

The wet adhesion test results obtained with latex paints containing the wet adhesion monomers of the present invention are shown in Table IV. Included for comparison are the paints containing no wet adhesion monomer ("P-L-0") and commerically available wet adhesion monomer SIPOMER® WAM II ("P-L-WII"). As stated above, the labels M1, M3, etc., refer to monomers corresponding to the Examples described herein.

TABLE IV

WET ADHESION RESULT

| Paint Formulation | 4-Hr Wet Adhesion Glidden 4554 Med. Green % Removed in 1000 cycles | 24-Hr Wet Adhesion Glidden 4554 Med. Green % Removed in 1000 cycles | 7-Day Wet Adhesion Glidden 4554 Med. Green % Removed in 1000 cycles |
|---|---|---|---|
| Example 12 | 100 | 100 | 100 |
| P-L-O No Wet Adhesion Monomer Example 13 | 0 | 0 | 0 |
| P-L-WII 1% SIPOMER WAM II Monomer Example 14 | 0 | 0 | 0 |
| P-L-W II 0.5% WAM I Example 15 | 0 | 0 | 0 |
| P-L-M1 1% Monomer Ml Example 16 | 0 | 0 | 0 |
| P-L-M1 0.5% Monomer M1 Example 17 | 100 | 55 | 10 |
| P-L-M1 0.1% Monomer M1 Example 18 | 100 | 80 | 15 |
| P-L-M2 1% Monomer M2 Example 19 | 25 | 15 | 10 |
| P-L-M3 1% Monomer M3 Example 20 | 100 | 100 | 5 |
| P-L-M6 1% Monomer M6 Example 21 | 0 | 0 | 0 |
| P-L-M7 1% Monomer M7 Example 22 | 65 | 0 | 0 |
| P-L-M8 1% Monomer M8 Example 23 | 15 | 0 | 0 |
| P-L-M9 1% Monomer M9 Example 24 | 100 | 50 | 25 |
| P-L-M10 1% Monomer M10 | | | |

The results in Table IV show that without the addition of the wet adhesion monomer, the paint fibers are completely removed regardless of the drying period and that the monomers of the present invention are equivalent to the commercially used monomer SIPOMER® WAM II at the levels tested.

What is claimed is:

1. A process for preparing blocked derivatives of m- or p-isopropenyl-α,α-dimethylbenzyl isocyanate comprising the steps of contacting:
    (i) a meta- or a para-isopropenyl-α,α- dimethylbenzyl carbamate ester;

(ii) an hydroxy functional blocking group selected from the group consisting of hydroxyethylethyleneurea, hydroxyethylpropyleneurea, dialkylaminoethanol and dialkylaminopropanol; and optionally (iii) a catalyst at a temperature and for a length of time sufficient to produce a blocked derivative of m- or p-isopropenyl-α,α-dimethylbenzyl isocyanate.

2. A process for preparing blocked derivatives of m- or p-isopropenyl-α,α-dimethylbenzyl isocyanate comprising the steps of contacting:

(i) a meta- or a para-isopropenyl-α,α-dimethylbenzyl carbamate ester;

(ii) an hydroxy functional blocking group selected from the group consisting of hydroxyethylethyleneurea, hydroxyethylpropyleneurea, dialkylaminoethanol and dialkylaminopropanol; and (iii) a catalyst, wherein the catalyst is at least one compound selected from the group consisting of $ZnCl_2$, $Zn(OCOCH_3)_2$, $FeCl_3$, cobalt acetate, chelates of transition metal ions with α,β-diketones and ketoesters, $SnCl_2$, $SnCl_4$, $SNO_2$, dibutyltin dilaurate, acetoxytetrabutylstannoxane, dimethyltin dilaurate, stannous octoate, dibutyltin oxide and tertiary amines, titanates such as tetraisopropyl titanate at a temperature and for a length of time sufficient to produce a blocked derivative of m- or p-isopropenyl-α,α-dimethylbenzyl isocyanate.

3. A process for preparing blocked derivatives of m- or p-isopropenyl-α,α-dimethylbenzyl isocyanate comprising the steps of contacting:

(i) a meta- or a para-isopropenyl-α,α-dimethylbenzyl carbamate ester;

(ii) an hydroxy functional blocking group wherein the hydroxy functional blocking group is selected from the group consisting of hydroxyethylethyleneurea, hydroxyethylpropyleneurea, dialkylaminoethanol and dialkylaminopropanol; and (iii) a catalyst which is a mixture of 1,3-diacetoxy-1,1,3,3-tetrabutyl distannoxane and didecylmethylamine at a temperature and for a length of time sufficient to produce a blocked derivative of m- or p-isopropenyl-α,α-dimethylbenzyl isocyanate.

* * * * *